(12) United States Patent
Zhang et al.

(10) Patent No.: US 8,414,873 B2
(45) Date of Patent: Apr. 9, 2013

(54) BLOOD VESSEL STENT OF AMIDOGLUCOSAN POLYSACCHARIDE LOADED WITH CD133 ANTIBODY AND ITS PREPARATION METHOD

(76) Inventors: Shixuan Zhang, Dalian (CN); Jinghan Sui, Dalian (CN); Hong Zhao, Dalian (CN); Dazhi Yang, Dalian (CN)

( * ) Notice: Subject to any disclaimer, the term of this patent is extended or adjusted under 35 U.S.C. 154(b) by 0 days.

(21) Appl. No.: 12/602,976

(22) PCT Filed: Oct. 10, 2008

(86) PCT No.: PCT/CN2008/072660
§ 371 (c)(1),
(2), (4) Date: Dec. 3, 2009

(87) PCT Pub. No.: WO2009/049550
PCT Pub. Date: Apr. 23, 2009

(65) Prior Publication Data
US 2010/0215712 A1    Aug. 26, 2010

(30) Foreign Application Priority Data
Oct. 10, 2007    (CN) .......................... 2007 1 0157449

(51) Int. Cl.
*A61K 31/74*    (2006.01)
*A61K 9/00*    (2006.01)
*A61F 2/00*    (2006.01)
*A01N 25/00*    (2006.01)

(52) U.S. Cl.
USPC ........ 424/78.03; 424/400; 424/423; 424/405; 623/1.42; 623/1.11; 623/1.45

(58) Field of Classification Search ........................ None
See application file for complete search history.

(56) References Cited

U.S. PATENT DOCUMENTS

| | | | |
|---|---|---|---|
| 5,705,270 A * | 1/1998 | Soon-Shiong et al. .... | 428/402.2 |
| 7,919,075 B1 * | 4/2011 | Michal et al. .............. | 424/78.03 |
| 7,955,512 B2 * | 6/2011 | Park et al. ................. | 216/58 |
| 2005/0267560 A1 * | 12/2005 | Bates ......................... | 623/1.1 |
| 2007/0123977 A1 | 5/2007 | Cottone, Jr. et al. | |
| 2010/0247603 A1 * | 9/2010 | Ge et al. .................... | 424/423 |
| 2011/0020232 A1 * | 1/2011 | Eberhart et al. ........... | 424/9.2 |

FOREIGN PATENT DOCUMENTS

| | | |
|---|---|---|
| CN | 1278743 | 1/2001 |
| CN | 1257753 | 5/2006 |
| CN | 101172168 | 8/2008 |

* cited by examiner

*Primary Examiner* — Michail Belyavskyi
(74) *Attorney, Agent, or Firm* — Squire Sanders (US) LLP

(57) ABSTRACT

A blood vessel metal stent coating of amidoglucosan polysaccharide loaded with antibody comprises carrier material composed of chitosan and inartificial degradable acidic amidoglucosan polysaccharide and the effective dose of CD133 antibody loaded in the carrier material. The blood vessel metal stent coating is manufactured with self-assemble method to fix the CD133 antibody in the carrier material of the coating. The coating has good biocompatibility, water retention property, flexibility, flush resistance and bio-stability, and can specifically capture the vascular endothelial progenitor cells in human peripheral blood, and differentiate into vascular endothelial cells. The process would accelerate endothelialization to repair injured vessel caused and prevent restenosis and thrombosis efficiently.

4 Claims, 3 Drawing Sheets

BLOOD VESSEL STENT OF AMIDOGLUCOSAN POLYSACCHARIDE LOADED WITH CD133 ANTIBODY AND ITS PREPARATION METHOD

FIELD OF THE INVENTION

The present invention relates to the field of medical devices implanted in vessels within the body. More particularly, it is a kind of metal vascular stent loaded with bio-antibody, which specifically capture the vascular endothelial progenitor cells in human peripheral blood, and differentiate into vascular endothelial cells.

BACKGROUND OF THE INVENTION

Coronary artery and peripheral vascular angiemphraxis is the most fatal factor for human health. Intravascular stenting has become one of the most effective therapy methods to release such diseases easily. After implantation, the first generation stent, bare metal stent, can cause inflammation, in the long stretch leading to intravascular intimal hyperplasia, and further stimulate the growth factor and cytokine secretion, leading to smooth muscle cell proliferation and migration, caused in-stent restenosis which occurs in about 15 to 30% of the procedures. The second generation drug eluting stent, such as rapamycin or paclitaxel stents, have dramatically reduced the incidence of in-stent restenosis and the incidence of adverse events. Anti-proliferation drug, interfere with the natural healing response by preventing or significantly delaying the formation of a functional endothelial lining over the stent, increasing the risk of the late in-stent thrombosis. Most drug-eluting stents use synthetic polymer matrices as coatings. Increasing evidence suggests that some adverse reactions, such as hypersensitivity reactions, inflammatory reactions and vascular intimal hyperplasia have been occurred and clinical therapy results suggest that drug-eluting stent might casuse late restenosis after operation. Drug coatings can inhibit the proliferation of smooth muscle cells and the regeneration of ECs, delaying the endothelialization of blood vessel and increasing the risk of late thrombosis. As shown in studies that using bare metal stent does not influence the physiological reaction of proximate and distal blood vessel of stent, but using drug eluting metal stents lead to paradoxical contraction of proximate and distal blood vessel of stent. The findings indicate that the diffusion of anti-proliferation drug on drug-eluting stents may cause injury of blood vessel endothelium, and may also be the cause of paradoxical reaction of blood vessel. The FDA reported 50 hypersensitivity reactions after stent placement for 6 months, such as tetter, dyspnoea, urticaria, pruritus, and febricity. The reports and autopsy findings suggest that systemic hypersensitivity reactions that, in some cases, have been associated with late thrombosis and death. An important uncertain factor in the efficacy of drug-eluting stent is the use of polymers.

In 1997, Asahara isolated vascular endothelial progenitor cells (EPCs) from human peripheral blood with anti-CD34 and anti-vascular endothelial growth factor 2 (VEGFR-2). In vitro, these cells differentiated into functional vascular endothelial cells (ECs). The in vivo results suggested that EPCs may contribute to neoangiogenesis in adult species, consistent with vasculogenesis, a paradigm otherwise restricted to embryogenesis[Science, 1997, 275 (5320):964]. In 2003, Toshihiko et al. have shown accelerated endothelialization on polyethylene terephthalate stent preclotted with autologous bone marrow cells having a subset of early ECs that express the CD34 antigen on their surfaces. The authors used composite stent implanted in the canine's descending thoracic aorta and carotid artery for 4 weeks. The study stent was treated with CD34+ bone marrow cells mixed with venous blood; the control stent was treated with ECs mixed with venous blood only. Histologic evaluation in one week demonstrated significant increases of surface endothelialization on the seeded stents (92%±3.4% vs 26.6%±7.6%) compared with controls. Four weeks later, on the seeded stents, there was a layer of neointima consisting of a single layer of ECs shown to be positive with VEGFR-2 and CD34+ staining on the surface. Most of the control stent surfaces were covered with a thin layer of pseudointima. There were no ECs on the pseudointima, which was largely composed of a fibrin coagulum with some red cells, macrophages, neutrophils, giant cells, and occasional α-actin positive cells. [Biomaterials 2003, 24:2295]

In 2005, Kutryk et al designed CD34 antibody (CD34) stent with the technology of isolating EPCs from human blood by magnetic bead selection on the basis of cell surface antigen expression. CD34 were immobilized to the stent surface with PTFE. [U.S. Pat. No. 7,037,332] The CD34 stent have been shown to exhibit cross-reactivity in porcine stent explants, which were observed to have a rich population of EPCs after only 48 hours. The third generation antibody coating stents have been developed using immobilized antibodies targeted at EPCs surface antigens. The early establishment of a functional endothelial layer after vascular injury has been shown to assist in the prevention of neointimal proliferation and thrombus formation. These preclinical and preliminary clinical results have to be interpreted carefully, considering the recent emergence of new technologies such as drug-eluting stent. Drug-eluting stent inhibit the inflammatory and proliferative process of the normal healing response, including the formation of a confluent endothelial layer on the stent. The EPCs capture stent induced the rapid establishment of a functional endothelial layer early in the healing response. [J. American College of Cardiology 2005, 45(10):1574] However, the CD34 carrier coating materials are synthetic fat-soluble materials such as PTFE or polyurethane. CD34 is immunoglobulin IgG1. PTFE was not well compatible with CD34. Stent coating was prepared by immersing the stent into PTFE tetrahydrofuran solution mixed with CD34, dipping to the surface of stent after emulsification. After drying, the natural state of protein secondary structure of CD34 gradually changed under the anhydrous environment. Therefore, this CD34 stent also can not have desirable biologic stability in a long period. Kutryk et al designed that CD34 was chemically crosslinked onto functional matrix coating on the metal stent. The major problem of chemical crosslinking is that partical effective sites of antibody are chemically crosslinked. The activity of CD34 is going to lose gradually without water in the coating. In addition, CD34 lacks specificity on EPCs, so the coating can adsorb EPCs and ECs which CD34+ at the same time. The PTFE matrix can not provide a suitable place for the differentiation of vascular ECs due to its poor biocompatibility. [Criculation Jul. 5, 2005, 12-17]

In 1997, Sheri Miraglia et al described the production of CD133 monoclonal antibody (CD133). CD133+ binds to a novel cell surface antigen present on CD34+ bright subset of human hematopoietic stem and progenitor cells, suggesting that it may be an important early marker for hematopoietic stem and progenitor cells. [Blood 90: 5002-5012; 5013-5021] Wang Mingyuan showed that in the process of CD34+/CD133+ EPCs differentiating into mature ECs in vitro, stem cell markers CD133+ has been gradually declining, which indicates that EPCs is in a transition phenotype stage from the blood stem cells to ECs. With the processes of differentiation and maturation, cell phenotypes are gradually changed by some gene regulation. CD34+ is the most common hematopoietic stem cell marker, expressing ECs line. CD133+ is a newly discovered stem cell marker, not expressing on mature ECs that distinction is the vascular ECs and EPCs the only marker. Therefore CD133+ is an earlier marker for expressing HSPCs than CD34+. HSPCs of CD133+/CD34+ and CD133−/CD34+ expressed stem cell (Stem cell expressed by HSPCs of CD133+/CD34+ and CD133−/CD34+) are about 0.080% and 0.034% in adult peripheral blood, respectively. CD34+ is expressed by EPCs, circulating ECs, common myeloid progenitor (myelomonocytic precursors, megakaryocytic/erythroid precursors) and common lymphoid progenitor. CD133+ is a more specific marker for expressing EPCs. In other mature blood cells, such as nucleated red blood cells, lymphocytes, myelocytic, mononuclear and platelets, CD133+ expressions were not detected. In other types of haemopoietic stem cells, CD133+ expression was not detected. Therefore, VEGFR-2 or CD34 is not the ideal choice for the EPCs capture, but CD133 is the more specific choice. [J. Clin Invest, 2002, 109:337]

The amidoglucosan polysaccharides in nature include basic amidoglucosan polysaccharides and acidic amidoglucosan polysaccharides, which can be degraded gradually by lysozyme in vivo. Chitosan (CH) is a linear polysaccharide, containing two β-1,4-linked 2-amino-2-deoxy-D-glucopyranose, obtained by partial de-N-acetylation of chitin, which has good biocompatibility, biodegradability and antimicrobality. CH has been approved by FDA to use as biodegradable surgical suture material. It can inhibit vascular smooth muscle cell proliferation, promote the growth of ECs and improve the wound healing. All the properties of CH described above demonstrated that CH can be applied in the field of stent coating material so as to prevent restenosis. [Acad. J. Sec. Mil. Med. Univ. 20 (1999) 962] In addition, carboxymethyl-chitosan is acidic amidoglucosan polysaccharide from carboxymethylation of CH with good biocompatibility, water retention capacity, flexibility, washing resestance, biological stability [Acad. J. Sec. Mil. Med. Univ. 15 (1994):452] There are basically six acidic amidoglucosan polysaccharides in nature, such as hyaluronic acid, heparin, chondroitin sulfate, dermatan sulfate, keratin sulfate. Hyaluronic acid (HA) is a ubiquitous component of extracellular matrix. HA is a linear polysaccharide containing two β-1,4-linked 2-amino-2-deoxy-D-glucopyranose. HA is a very important glycosamineglycan in human tissue. It has become an important medical biopolymer material and has been widely used in medical bioengineering. In 2005, HA as wound dressing was approved by FDA. [Primaphamr] HA shows high affinity for injured tissue to provide suitable environment for cell proliferation and differentiation, promoting cell growth, differentiation, reconstruction and rehabilitation. Especially HA can promote ECs proliferation and angiogenesis in blood vessel of human and mammalian as coating of endovascular devices. HA has been shown to inhibit platelet aggregation and adhesion and to prolong the bleeding time. Because of its antithrombotic effects and its known coating abilities, HA may provide a potential biocompatible and thromboresistant coating for endovascular devices to anticoagulated blood under arterial blood flow conditions. These properties make HA an excellent material for fabricating stent coatings to provide an artificial extracellular matrix environment suitable for encapsulated cells differentiation to prevent restenosis. [J. Biomed Mater Res, 2000, 05:101-109; International Congress Series, 2001, 1223:2279-2284; Biomacromolecules 2003, 4:1564-1571]

The ideal stent coatings should have good biocompatibility, accelerating promoting injured tissue healing, preventing excessive proliferation, accelerating vascular endothelium, preventing thrombosis and restenosis, and also should have biological stability. In this invention, layer-by-layer self-assembly two polysaccharides, HA and CH, were employed to multilayer coating loading with CD133 for endovascular stent. After implanting this stent in vessel, EPCs of the peripheral blood can be captured specifically by CD133, then differentiated into ECs. Amidoglucosan polysaccharides have good biocompatibility, which provides suitable location for the differentiation of EPCs into ECs and monolayer ECs overburden layer on stent can form in 48 h, which can effectively avoid the formation of partial "pseudointima". This would repair accelerative vessel injury caused by stent expanding and would be a more natural way to prevent restenosis and thrombosis.

SUMMARY OF THE INVENTION

The invention provides that a blood vessel metal stent coating of amidoglucosan polysaccharide loaded with antibody comprises carrier material composed of chitosan and inartificial degradable acidic amidoglucosan polysaccharide and the effective dose of CD133 loaded in the carrier material. The blood vessel metal stent coating is manufactured with self-assemble method to fix the CD133 in the carrier material of the coating. The coating has good biocompatibility, water retention property, flexibility, flush resistance and bio-stability, and can specifically capture EPCs in human peripheral blood, and differentiate into ECs. The process would accelerate endothelialization to repair injured vessel caused and prevent restenosis and thrombosis efficiently.

The Solutions of the Invention are as Follows:

A coating of amidoglucosan polysaccharide loaded with CD133 used on metal vascular stent, wherein chitosan comprises 25-70% of its weight, amidoglucosan polysaccharide 30-75% and CD133 0.000001-0.01%.

Wherein, the CD133 is from monoclonal antibody or polyclonal antibody, and the monoclonal antibody or polyclonal antibody reacts with the vascular endothelial progenitor cells (EPCs) surface CD133+ specifically.

Wherein, the acidic amidoglucosan polysaccharide is from hyaluronic acid, heparin, chondroitin sulfate or carboxymethyl-chitosan.

The preparation method for the coating, comprising the steps of: on the vascular stent surface of 316L stainless steel or nickel-titanium alloys, the multilayer construct was accomplished with electrostatic self-assembled process by sequential dip-coating of the substrate in alternating between 0.1-5.0% acidic amidoglucosan polysaccharide solution (weight/volume) and 0.1-5.0% CH solution (weight/volume), followed by a wash with a flow of water and a dry with hot air before repeating the above procedures for 5-15 times and making the thickness of the coating to 50-150 nanometer, then dip-coating mixed solution with 0.1-5.0% acidic amidoglucosan polysaccharide solution (weight/volume) and 0.0001-0.1% CD133 solution (weight/volume) (volume ratio 1:1), then washing with water, air dried, stored at 4° C.

Another preparation method for the coating, comprising the steps of: on the vascular stent surface of 316L stainless steel or nickel-titanium alloys, the multilayer construct was accomplished with a self-assembled process by sequential dip-coating of the substrate in alternating between 0.1-5.0% acidic amidoglucosan polysaccharide solution (weight/volume) and 0.1-5.0% CH solution (weight/volume), followed by a wash with a flow of water and a dry with hot air, before repeating the above procedures for 5-15 times and making the thickness of the coating to 50-150 nanometer, then dip-coating 0.1-5.0% acidic amidoglucosan polysaccharide solution (weight/volume), followed by dip-coating 0.001-0.1% 1-(3-dimethy laminopropyl)-3-ethylcarbodiimide hydrochloride (EDC) solution (weight/volume) for 10-30 minutes, taking it out and dip-coating 0.0001-0.1% CD133 solution (weight/volume), washing with water, air dried, stored at 4° C.

DETAILED DESCRIPTION OF THE INVENTION

Coating by Electrostatic Self-Assemble Method

CH is a linear alkaline amidoglucosan polysaccharide of β-1,4-linked 2-amino-2-deoxy-D-glucopyranose. HA is a linear acidic amidoglucosan polysaccharide of a alternating N-acetyl-β-D-glucosamine and β-D-glucuronic acid residues linked (1→3) and (1→4), respectively. CD133 is immunoglobulin IgG1, and a water-soluble proteoglycan. CD133 can form negative ion and CH can form positive ion in PBS (pH7.4). Amidoglucosan polysaccharide and CD133 was well compatible with each other in the aspect of biological evaluation. The multilayer construction was expected to greatly modify the wettability of the substrate. The multilayer construction loaded with CD133 by electrostatic self-assemble.

observing it under fluorescence microscope, with red fluorescence. It suggests that the outer layer of the coating is negative ion.

Detection of Surface Character of Fundamental Coating

X-ray diffraction analysis showed that the thickness of each bilayer and $HA(CH/HA)_7$ coatings were approximately 14.4 nanometer (nm) and 100 nanometer, respectively. The atomic mechanical 3D microscope scanning results of fundamental coating: line roughness Ra 2.528 nm, Rp 3.188, Rmax 16.416; surface roughness Ra 2.556 nm, Rp 3.218, Rmax 53.236. Uniformly dense island arrangement was observed on the coatings by atomic mechanical 3D scanning microscope. It indicated that this kind of coatings surface could improve both corrosion resistance and antithrombogenicity. Dipping fundamental coating, antibody coating and antibody solution on the surface of 316L stainless metal disk, the result of infra red spectrum indicated that there was a lot of water in the antibody coating and the infra red spectrum was consistent with antibody solution, which indicated that the antibody in antibody coating still remained its natural protein secondary active structure.

Detection of Amidoglucosan Polysaccharides in Coating

Preparation of Reference Standard Solution: Adding Some Water into Appropriate glucosamine hydrochloride reference

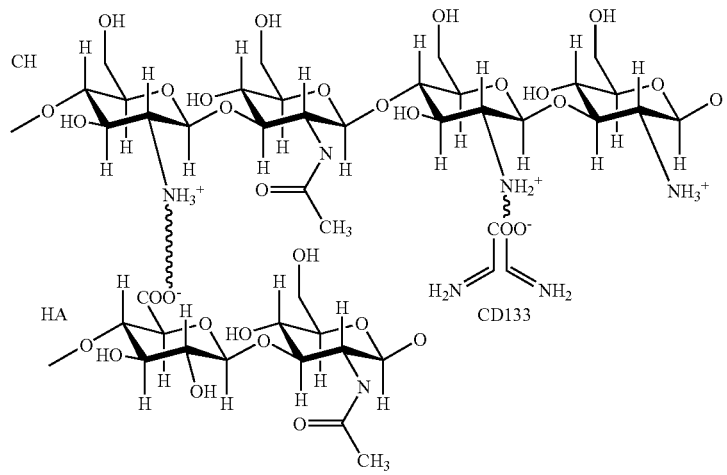

Detection of Electrostatic Self-Assembled Fundamental Coating:

(1) The outer layer of fundamental coating is CH—$NH_3^+$ on 316L stainless steel disk. It was dropped into positive ion cyanine fluorescent dye solution for 5 minutes and washed several times with PBS solution, then observing it under fluorescence microscope, without red fluorescence. When putting it in negative ion cyanine fluorescent dye solution for 5 minutes and washing it several times with PBS solution, then observed it under fluorescence microscope, with red fluorescence. It suggests that the outer layer of the coating is positive ion.

(2) The outer layer of fundamental coating is HA-COO— on 316L stainless steel disk. It was dropped into negative ion cyanine fluorescent dye solution for 5 minutes and washed several times with PBS solution, then observed under fluorescence microscope, without red fluorescence. When putting it in positive ion cyanine fluorescent dye solution for 5 minutes and washing it several times with PBS solution, then standard, making it concentration 10 μg/ml. Preparation of Sample Solutin: Putting the Stent to be Detected into a Bottle (with a stopper and 0.5 ml 0.1 mol/L hydrochloric acid solution in it), after ultrasonic washing for 30 seconds, taking the stent out of the bottle; then putting it into B bottle (with a stopper and 0.5 ml 0.1 mol/L sodium hydroxide solution in it), after ultrasonic washing for 30 seconds, taking the stent out of the bottle; ultrasonic washing circularly in A and B bottles for 10 times by turns. Putting solution in A and B bottles together, then into a tube with stopper. Adding 1 ml concentrated hydrochloric acid, filling nitrogen, closing the stopper and heating the tube for 1 hour in water bath. Using sodium hydroxide saturated solution to neutralize the mixed solution to neutrality after the temperature falling to room temperature.

To take sample solution into 5 ml volumetric flask, adding acetylacetone solution 0.5 ml, closing the stopper and heating the volumetric flask for 30 minutes in water bath. To add p-dimethylaminobenzene solution 0.5 ml after the temperature falling to room temperature, then adding water to the scale and shaking. Showing pink and maximum absorption wavelength is in 530 nm. Besides putting glucosamine hydrochloride reference standard solution 3 ml into a 5 ml volumetric flask. Detection in the same way and then there is the result. [Pharmaceutical Analysis, 5th edition, People's Health Publishing House, 2003, P329, 282]

Evaluation of the Biocompatibility of (CH/HA)n Coatings

Further insights of the biocompatibility of HA(CH/HA)$_n$ coating disks were obtained through platelets adhesion test in vitro. Briefly, fresh blood was drawn from healthy, medication-free volunteers. HA(CH/HA)$_n$ disk was dipped into 25 ml freshly prepared platelet solution. The platelet adhesion was allowed to proceed for 1 hour with gentle shaking. After incubation, the samples were recovered and washed 3 times with PBS. Finally, the amount of platelets was determined using scanning electron microscopy (SEM).

Biocompatibility of HA(CH/HA)n Coatings: the platelet adhesion of HA(CH/HA)$_n$ coatings was proceed for 1 hour. SEM results illustrated in FIG. 1 showed that: compared with bare 316L stainless steel disk, the adhesion of human blood platelet was decreased as long as the layer thicknesses increase. The adhesion was barely determined when the number of layer achieved seven. HA(CH/HA)$_7$ coatings effectively reduced the adhesion of human blood platelet and pseudo-foot production, as well as improving the biocompatibility of the metal surface.

Evaluation of (CH/HA)$_7$/CH/CD133 Coatings on EPCs Capture In Vitro

The ability of the (CH/HA)$_7$/CH/CD133 stent to capture EPCs was assessed in a model in vitro. Fresh peripheral human anticoagulant blood 20 ml was centrifuged at 2000×g for 10 minutes to isolate cells, and then the supernatant was collected. (CH/HA)$_7$/CH/CD133 stent was inserted into the supernatant at 37° C. for 1 hour, washed 3 times with PBS, and then analyzed by SEM. The results illustrated in FIG. 2 showed that CD133 could specially capture EPCs quickly in peripheral blood.

Immunohistochemical Analysis of CD133

(CH/HA)n/CH/CD133 stent was inserted into Mo IgG (H+L)/FITC antibody solution at 37° C. incubation for 30 minutes, washed with PBS, and observed by fluorescent confocal microscopy. The results illustrated in FIG. 3 showed that: CD133 shows green color fluorescence.

Uniformity and Stability of (CH/HA)$_7$/CH/CD133 Stent: the distribution of CD133 was determined by immunohistochemical analysis, in FIG. 3. The results indicated that the distribution of CD133 was uniformly coated over entire stent surface. The distributions and intensity of green color fluorescence showed no evident changes on the condition that (CH/HA)$_7$/CH/CD133 stents were cyclorotated in PBS at 37° C. for 1 h, or stored for 1 years at 5-10° C. The results demonstrated that resistance of underscouring and bioactivity of the loaded CD133 on the designed stent were both satisfied.

The SEM results illustrated in FIG. 2 showed that only considerable EPCs of 7-8 nm spheroid cells were captured on the surface of (CH/HA)$_7$/CH/CD133 coated disk, without platelet or any other types of cell adhesion.

Evaluation of (CH/HA)n/CH/CD133 Stents on EPCs Capture and Differentiation In Vivo (CH/HA)$_7$/CH/CD133 stents were implanted in arteria auricularis of rabbits. Rabbits were sacrificed at 1 h, 24 h and 48 h after implantation. The arteries were explanted with 1 cm of non-stented vessel proximal and distal to the stent, and then washed with PBS. Finally, (CH/HA)n/CH/CD133 stents were performed with anti-human VEGFR-2 polyclonal antibody solution for 30 min. The stents were washed with PBS, incubated in Rb IgG (H+L)/TRITC antibody solution at 37° C. 30 min later, washed with PBS, and observed under fluorescent confocal microscopy. EPCs or ECs show red color fluorescence.

The results showed that: within 1 h, 24 h and 48 h in auricular arteries of rabbits affer stents implantation, about 10%, 65% and 85% of the stent surface (FIGS. 4, 5, 6) was covered with red fluorescence, respectively. Furthermore, some part of the implanted stent was covered with integrated endothelial layer, which indicated that EPCs started to differentiate in vivo. The experimental results showed that: (CH/HA)$_7$/CH/CD133 coating specifically captured EPCs in the peripheral blood. The captured EPCs then differentiated into ECs by the induction of vascular endothelial growth factor. It demonstrated that the polysaccharide coating provided appropriate conditions for the proliferation and differentiation of EPCs.

Overview

Compared with existing technology, the maximal feature and effect of this invention are:

(1) This invention chooses natural and biodegradable amidoglucosan polysaccharides as carrier material and firstly introduces the idea of loading CD133 on the nano-coating of metal vascular stent by electrostatic self-assembled technology. The stent has good biocompatibility, water retention capacity, flexibility, washing resistance, biological stability and can meet the need of goods shelf life, so it can be commercialized in large scale.

(2) In this invention, when the CD133 coating metal vascular stent has been implanted into blood vessel, it can specifically capture EPCs in human peripheral blood. The good biocompatibility of amidoglucosan polysaccharides provides suitable location for the differentiation of ECs. In two days, the surface of the stent will be covered with differentiated monolayer ECs, which can effectively avoid the formation of partial "pseudointima". Patients do not have to take antirejection drugs and fast endothelialization of stent and quick recovery and healing of damaged tissue can come true. It is a more natural and safer new measure to avoid the formation of thrombus and restenosis

EXPERIMENTAL EXAMPLES

Example 1

Figure 1:
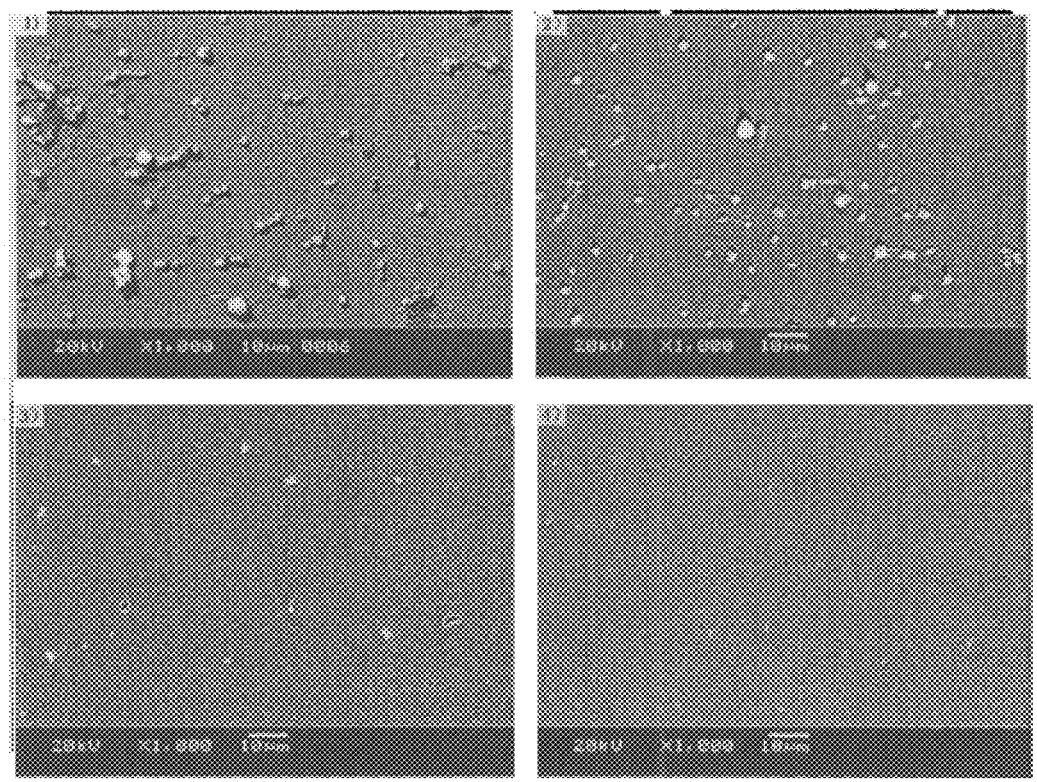
FIG. 1 shows SEM images of adhered platelets on 1) mechanical polishing 316L steel sheet, 2) HA(CH/HA)$_2$, 3) HA(CH/HA)$_4$, 4) HA (CH/HA)$_7$.
Figure 2:
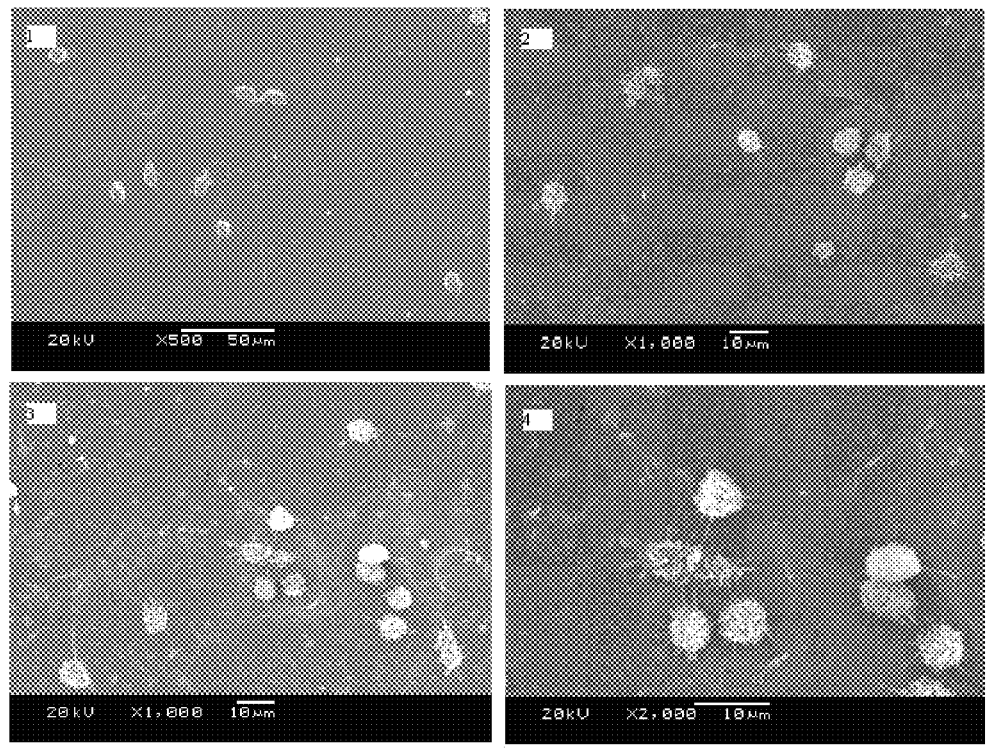
FIG. 2 shows SEM images of (CH/HA)$_7$/CH/CD133 on 316L steel disks which were cultured in vitro human peripheral blood at 37° C. for 1 hour. The magnification times was 1) 500×, 2) 1000×, 3) 1000×, 4) 2000×. The shallow needling cells illustrated were captured EPCs.
Figure 3:
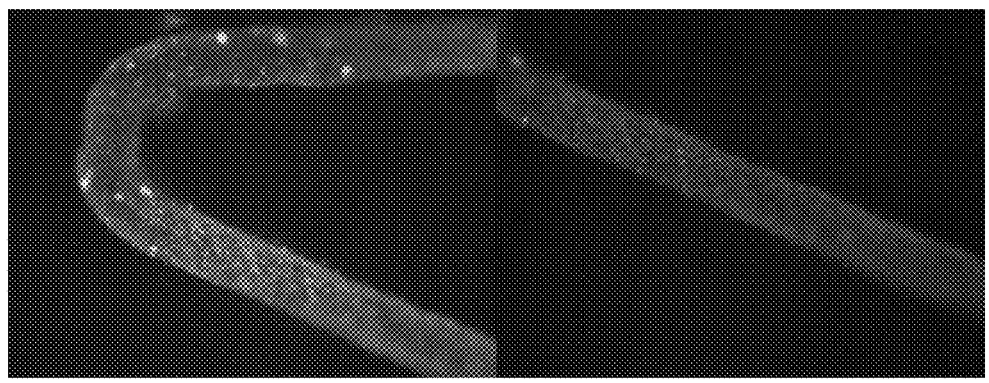
FIG. 3 show fluorescence image of (CH/HA)$_7$/CH/CD133 coating on 316L steel stent phenotyped, with Mo IgG (H+L)/FITC antibody.
Figure 4:
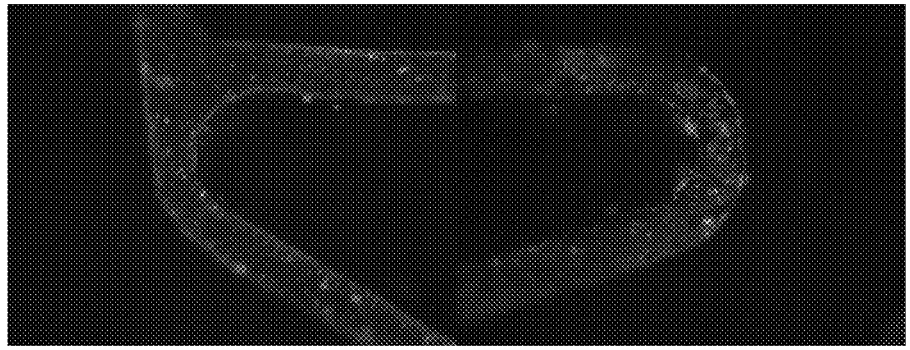
FIG. 4 show fluorescence images of (CH/HA)$_7$/CH/CD133 stents implanted in rabbit artery, 1 h, with anti-human VEGFR-2 polyclonal antibody, and then with Rb IgG (H+L) TRITC antibody.
Figure 5:
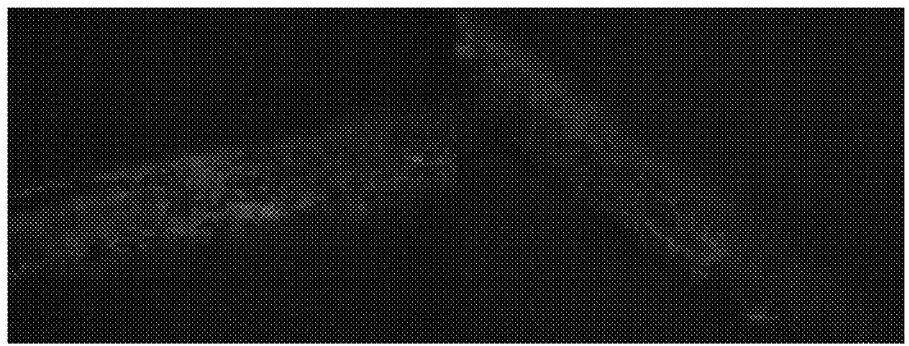
FIG. 5 show fluorescence images of (CH/HA)$_7$/CH/CD133 stents implanted in rabbit artery, 24 h, with anti-human VEGFR-2 polyclonal antibody, and then with Rb IgG (H+L) TRITC antibody.
Figure 6:
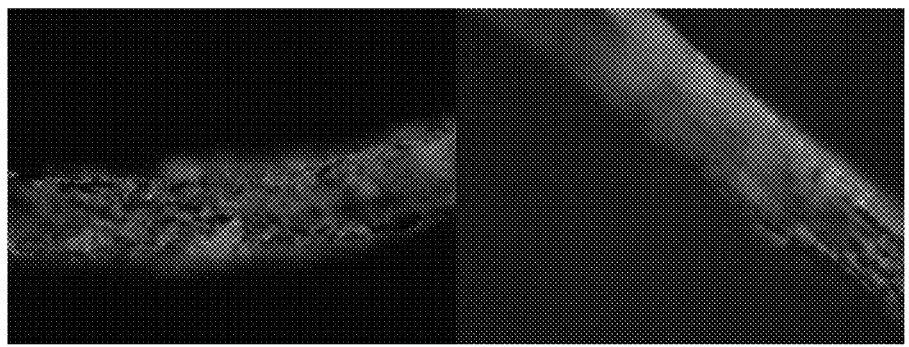
FIG. 6 show fluorescence images of (CH/HA)$_7$/CH/CD133 stents implanted 1) in vitro, 48 h, with anti-human VEGFR-2 polyclonal antibody, and then with Rb IgG TRITC antibody.

On the vascular stent surface of 316L stainless steel, the multilayer construct was accomplished with a electrostatic self-assembled process by sequential dip-coating of the substrate in alternating between 1.0% sodium HA solution and 1.0% CH solution, followed by a wash with a flow of water and a dry with hot air before repeating the above procedures for 7 times, then dipping 1.0% sodium hyaluronate solution, then washing with water, air dried, stored at 4° C.

Example 2

On the vascular stent surface of 316L stainless steel, the multilayer construct was accomplished with a electrostatic self-assembled process by sequential dip-coating of the substrate in alternating between 1.0% sodium HA solution and 0.5% CH solution, followed by a wash with a flow of water and a dry with hot air before repeating the above procedures for 7 times, then dip-coating mixed solution with 1.0% sodium hyaluronate solution and 0.001% CD133 monoclonal antibody solution (volume ratio 1:1), then washing with water, air dried, stored at 4° C.

Example 3

On the vascular stent surface of nickel-titanium alloys, the multilayer construct was accomplished with a electrostatic self-assembled process by sequential dip-coating of the substrate in alternating between 1.5% sodium HA solution and 1.0% CH solution, followed by a wash with a flow of water and a dry with hot air before repeating the above procedures for 7 times, then dip-coating mixed solution with 1.5% sodium HA solution and 0.0005% CD133 polyclonal antibody solution (volume ratio 1:1), then washing with water, air dried, stored at 4° C.

Example 4

On the vascular stent surface of 316L stainless steel, the multilayer construct was accomplished with a electrostatic self-assembled process by sequential dip-coating of the substrate in alternating between 1.5% sodium heparin solution and 1.5% CH solution, followed by a wash with a flow of water and a dry with hot air before repeating the above procedures for 7 times, then dip-coating mixed solution with 1.5% sodium heparin solution and 0.0007% CD133 solution (volume ratio 1:1), then washing with water, air dried, stored at 4° C.

Example 5

On the vascular stent surface of 316L stainless steel, the multilayer construct was accomplished with a electrostatic self-assembled process by sequential dip-coating of the substrate in alternating between 1.0% sodium carboxymethyl-chitosan solution and 1.0% CH solution, followed by a wash with a flow of water and a dry with hot air before repeating the above procedures for 7 times, then dip-coating mixed solution with 1.0% sodium carboxymethyl-chitosan solution and 0.02% CD133 solution (volume ratio 1:1), then washing with water, air dried, stored at 4° C.

Example 6

On the vascular stent surface of 316L stainless steel, the multilayer construct was accomplished with a electrostatic self-assembled process by sequential dip-coating of the substrate in alternating between 1.0% sodium hyaluronate solution and 0.5% CH solution, followed by a wash with a flow of water and a dry with hot air before repeating the above procedures for 8 times, then dipping 1.0% sodium hyaluronate solution, followed by dip-coating 0.01-0.1% 1-(3-dimethylaminopropyl)-3-ethylcarbodiimide hydrochloride (EDC) solution (weight/volume) for 15 minutes, taking it out and dip-coating 0.005% CD133 solution, washing with water, air dried, stored at 4° C.

We claim:

1. A coating for a metal vascular stent, comprising chitosan, acidic amidoglucosan polysaccharide, and CD133 antibody, wherein chitosan comprises 25-70% of the weight of the coating, acidic amidoglucosan polysaccharide comprises 30-75% of the coating, and CD133 antibody comprises 0.000001-0.01% of the weight of the coating,
   wherein the coating is has a multilayer construct that comprises at least one layer formed of CD133 antibody and alternating layers of at least one layer formed of chitosan and at least one layer formed of the acidic amidoglycosan polysaccharide.

2. The coating of claim 1, wherein the CD133 antibody is from monoclonal antibody or polyclonal antibody, which reacts with the vascular endothelial progenitor cells (EPCs) surface antigen CD133.

3. The coating of claim 1, wherein the acidic amidoglucosan polysaccharide is from hyaluronic acid, heparin, chondroitin sulfate or carboxymethyl-chitosan.

4. The coating of claim 2, wherein the acidic amidoglucosan polysaccharide is from hyaluronic acid, heparin, chondroitin sulfate or carboxymethyl-chitosan.

* * * * *

UNITED STATES PATENT AND TRADEMARK OFFICE
CERTIFICATE OF CORRECTION

| | | |
|---|---|---|
| PATENT NO. | : 8,414,873 B2 | Page 1 of 1 |
| APPLICATION NO. | : 12/602976 | |
| DATED | : April 9, 2013 | |
| INVENTOR(S) | : Shixuan Zhang | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 299 days.

Signed and Sealed this
Eighteenth Day of February, 2014

Michelle K. Lee
*Deputy Director of the United States Patent and Trademark Office*